(12) United States Patent
LeCronier et al.

(10) Patent No.: US 8,287,540 B2
(45) Date of Patent: Oct. 16, 2012

(54) EASILY IMPLANTABLE AND STABLE NAIL-FASTENER FOR SKELETAL FIXATION AND METHOD

(75) Inventors: David LeCronier, Oxford, MI (US); Patrick Atkinson, Grand Blanc, MI (US)

(73) Assignee: Kettering University, Flint, MI (US)

( * ) Notice: Subject to any disclaimer, the term of this patent is extended or adjusted under 35 U.S.C. 154(b) by 178 days.

(21) Appl. No.: 12/818,395

(22) Filed: Jun. 18, 2010

(65) Prior Publication Data

US 2011/0313420 A1   Dec. 22, 2011

(51) Int. Cl.
*A61B 17/56* (2006.01)
*A61B 17/58* (2006.01)
*A61F 2/30* (2006.01)

(52) U.S. Cl. .......................................... 606/62; 606/64

(58) Field of Classification Search ................... 606/53, 606/60, 62–64, 65–68, 96, 98, 104, 105; 623/16.11, 18.11, 19.11
See application file for complete search history.

(56) References Cited

U.S. PATENT DOCUMENTS

| | | | |
|---|---|---|---|
| 5,454,813 A | 10/1995 | Lawes | |
| 5,472,444 A * | 12/1995 | Huebner et al. | 606/64 |
| 6,235,031 B1 | 5/2001 | Hodgeman et al. | |
| 6,355,043 B1 | 3/2002 | Adam | |
| 7,569,055 B2 | 8/2009 | Zander et al. | |
| 7,722,611 B2 | 5/2010 | Cavallazzi et al. | |
| 2004/0147930 A1 | 7/2004 | Zander et al. | |
| 2005/0075637 A1 | 4/2005 | Semet | |
| 2006/0084997 A1* | 4/2006 | Dejardin | 606/62 |
| 2009/0326533 A1 | 12/2009 | Dell'Oca | |

OTHER PUBLICATIONS

Angular Stable Locking System (ASLS); Dated Oct. 2008; 48 Pages; Synthes (www.synthes.com/lit).
The Titanium Solid Humeral Nail System Technique Guide; Dated 2001; 70 Pages; Synthes (www.synthes.com/lit).
Comparison of a New Braid Fixation System to an Interlocking Intramedullary Nail for Tibial Osteotomy Repair in an Ovine Model; Yan Lu et al.; Copyright 2009; 10 Pages; The American College of Veterinary Surgeons.
Angle Stable Locking Reduces Interfragmentary Movements and Promotes Healing After Unreamed Nailing; K. Kasper et al.; Dated Sep. 2005; 11 Pages; The Journal of Bone & Joint Surgery (www.ejbjs.org).
International Search Report, dated Feb. 10, 2012 5 Pages.

* cited by examiner

*Primary Examiner* — Eduardo C Robert
*Assistant Examiner* — Christina Negrelli
(74) *Attorney, Agent, or Firm* — Dickinson Wright PLLC

(57) ABSTRACT

An intramedullary nail (20) for insertion into the medullary canal (26) in a bone (24) surrounded by the cortex (28) and defines a bore (34) extending transverse to the intramedullary nail (20). A threaded fastener (22) extends along a fastener axis (A) and has a compression portion (48) having a compression portion diameter ($D_{CP}$), and a threaded portion (50) having a threaded portion diameter ($D_{TP}$) extending through a near cortex hole (40) and a far cortex hole (42), both holes (40, 42) radially overlapping the bore (34) and the threaded portion diameter ($D_{TP}$) threadedly engaging the bore (34). A compression transmission device (54) has an exterior (56) and an interior (58) and defines an interior space for transmitting the compressional load of the threaded fastener (22) to the intramedullary nail (20). The threaded fastener (22) extends through the compression transmission device (54) and the intramedullary nail (20) and the far cortex hole (42) for threadedly engaging the bore (34) and fixating the intramedullary nail (20) within the medullary canal (26). The interior space of the compression transmission device (54) is greater than the compression portion diameter ($D_{CP}$) of the fastener (22) for providing space at least partially about the threaded fastener (22) for allowing the fastener axis (A) to be variously disposed relative to the interior space.

27 Claims, 4 Drawing Sheets

EASILY IMPLANTABLE AND STABLE NAIL-FASTENER FOR SKELETAL FIXATION AND METHOD

STATEMENT REGARDING FEDERALLY SPONSORED RESEARCH

This invention was made with Government support under contract numbers W81XWH0720119 and W81XWH1120128 awarded by the Unites States Army Medical Research Acquisition Activity. The Government has certain rights in this invention.

BACKGROUND OF THE INVENTION

1. Field of the Invention

An easily implantable and stable nail-fastener for skeletal fixation to treat bone fractures and to provide support to the long bones and a method for implanting the nail-fastener.

2. Description of the Prior Art

An intramedullary nail for skeletal fixation of the type to which the subject invention pertains includes a threaded fastener extending through a compression transmission device to threadedly engage the nail. The compression transmission device transmits the compressional load of the threaded fastener to the intramedullary nail during fixation. One such nail-fastener device is illustrated in U.S. Patent Application No. 2009/0326533 to Dell'Oca, which discloses a two-diameter, two-piece locking bolt. The smaller diameter portion or male part of the bolt screws into the larger diameter portion or female part of the bole and threadedly engages the nail. The female part of the two diameter locking bolt abuts the nail to establish compression between the bolt and the nail. The prior art design requires the male part to be coaxial with the female part and near hole of the cortex in the bone. Additionally, there is interdigitation of the male and female parts, thus, they are not independent of one another.

SUMMARY OF THE INVENTION AND ADVANTAGES

The invention provides for an intramedullary nail-fastener characterized by a compression transmission device having an interior space being greater than the compression portion diameter of the fastener for providing space at least partially about the fastener for allowing the fastener axis to be variously disposed relative to the interior space.

The invention also provides a method of implanting such an intramedullary nail-fastener characterized by the step of providing the compression transmission device with the interior space being greater than the compression portion diameter of the fastener for providing space at least partially about the threaded fastener for allowing the fastener axis to be variously disposed relative the interior space.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
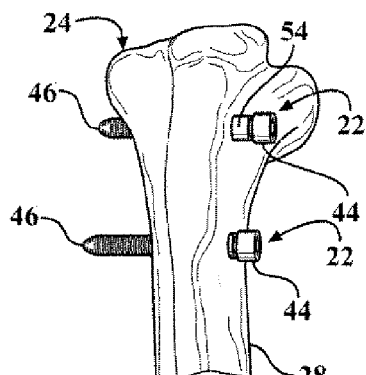
FIG. 1 is a side perspective view showing the nail-fastener of the subject invention.
Figure 3:
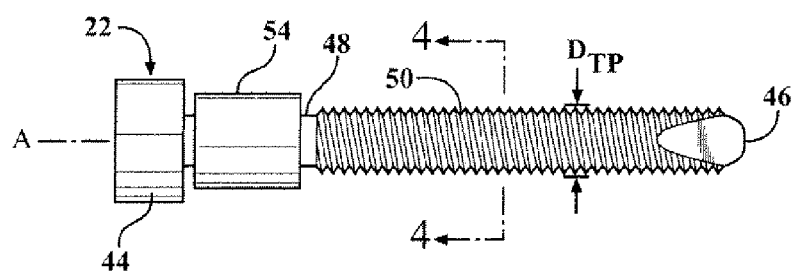
FIG. 3 is a side view of a fastener extending through the compression transmission device.
Figure 4:
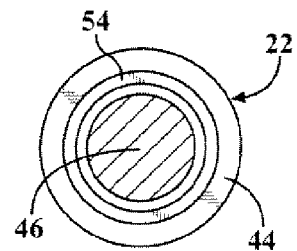
FIG. 4 is a cross-sectional view taken along line 4 of FIG. 3.

Referring to the Figures, wherein like numerals indicate corresponding parts throughout the several views, a intramedullary nail 20 and fasteners 22 for skeletal fixation constructed in accordance with the subject invention is shown in FIGS. 1-14.

The nail-fastener construct includes an intramedullary nail 20 for insertion into a bone 24 having a bone diameter $D_{BN}$ and including a medullary canal 26 surrounded by a cortex 28. The intramedullary nail 20, generally indicated, extends longitudinally in the medullary canal 26 of the bone 24 between a top end 30 and a bottom end 32 thereof and defines a bore 34 disposed transverse to, i.e., extending across but is not necessarily perpendicular to, the intramedullary nail 20. The intramedullary nail 20 may be straight, have an acute sharp bend, be bowed, or spiraled. The bore 34 is threaded and has a bore axis B extending between the near opening 36 and the far opening 38 transverse to the intramedullary nail 20. The bore 34 has a bore diameter $D_{BR}$ including a central bore diameter $D_{CBR}$ disposed centrally between the near opening 36 and the far opening 38 of the bore 34. The intramedullary nail 20 may define a plurality of bores 34 as needed.

The cortex 28 of the bone 24, generally indicated, includes a near cortex hole 40 and a far cortex hole 42 both radially overlapping the bore 34. The near cortex hole 40 has a near cortex hole diameter $D_{NC}$ and the far cortex hole 42 has a far cortex hole diameter $D_{FC}$, the near cortex hole diameter $D_{NC}$ being greater than the far cortex hole diameter $D_{FC}$ and the far cortex hole diameter $D_{FC}$ being equal to the central bore diameter $D_{CBR}$ in the preferred embodiment, as illustrated. However, it may be appreciated that the far cortex hole diameter $D_{FC}$ may be unequal to the central bore diameter $D_{CBR}$. The near cortex hole diameter $D_{NC}$ can be coaxial with the central bore diameter $D_{CBR}$, or skewed and offset in relation to the central bore diameter $D_{CBR}$. The far cortex hole 42 can be coaxial with the central bore diameter $D_{CBR}$, or skewed in relation to the central bore diameter $D_{CBR}$.

Figure 12:
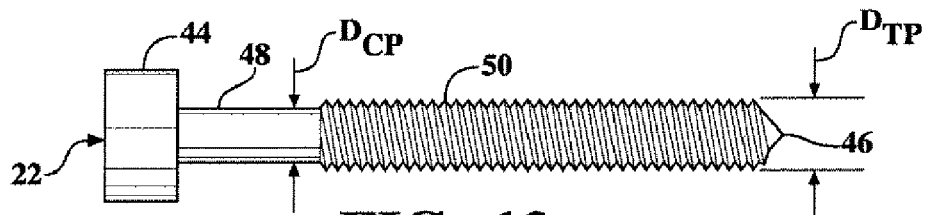
FIG. 12 is a side view of the fastener with the compression portion being unthreaded between the head and the threaded portion.
Figure 13:
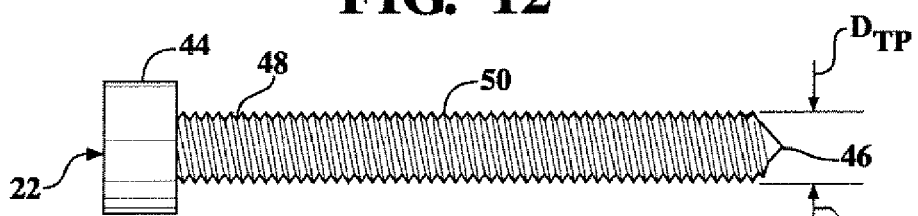
FIG. 13 is a side view of the fastener with the compression portion having threads continuing into the threaded portion.
Figure 14:
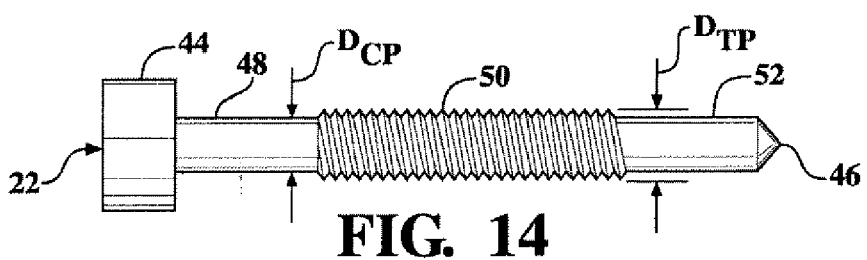
FIG. 14 is a side view of a centrally threaded fastener.

The threaded fastener 22, generally indicated, includes a head 44 and an end 46 with a compression portion 48 and a threaded portion 50 extending along a fastener axis A therebetween. The compression portion 48 of the threaded fastener 22 has a compression portion diameter $D_{CP}$ and the threaded portion 50 of the threaded fastener 22 has a threaded portion diameter $D_{TP}$. The compression portion diameter $D_{CP}$ may be smaller than or equal to the threaded portion diameter $D_{TP}$. The threaded portion diameter $D_{TP}$ is equal to the far cortex hole diameter $D_{FC}$ and the central bore diameter $D_{CBR}$ in the preferred embodiment, as illustrated, although it may be appreciated that the threaded portion diameter $D_{TP}$ may be unequal to the far cortex hole diameter $D_{FC}$ and the central bore diameter $D_{CBR}$. As shown in FIGS. 12 and 14, the compression portion 48 of the fastener 22 may be unthreaded between the head 44 and the threaded portion 50. As shown in FIG. 13, the compression portion 48 of the fastener 22 may be threaded with threads continuing into the threaded portion 50. As shown in FIG. 14, the fastener 22 can also include a compression portion 48 that is unthreaded and a second unthreaded portion 52 adjacent to the end 46, i.e., a centrally threaded fastener 22, which would eliminate thread purchase with the far cortex hole 42 and improve ease of fastener 22 removal. A plurality of threaded fasteners 22 at various orientations may be utilized as needed. Providing a threaded fastener 22 with a threaded portion diameter $D_{TP}$ being equal to the central bore diameter $D_{CBR}$ results in a highly stable construct free of toggle. The enlarged near cortex hole 40 eliminates binding during fastener 22 insertion.

The threaded fastener 22 extends through a compression transmission device 54 and the intramedullary nail 20 and the far cortex hole 42 so as to extend transversely to the intramedullary nail 20 for threadedly engaging the bore 34 and fixating the intramedullary nail 20 within the medullary canal 26. The compression transmission device 54 contacts the near cortex hole 40 for preventing movement of the compression transmission device 54 relative to the near cortex hole 40.

The compression transmission device 54, generally indicated, includes an exterior 56 having an exterior diameter $D_E$ and an interior 58 having an interior diameter $D_I$ defining an interior space. The exterior diameter $D_E$ of the compression transmission device 54 should be carefully considered to allow for a sufficient fastener 22 diameter for sufficient mechanical strength, but be small enough so that the bone 24 is not excessively weakened.

Figure 7A:
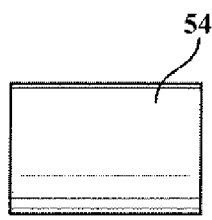
FIG. 7A is a side view of the compression transmission device.
Figure 7B:
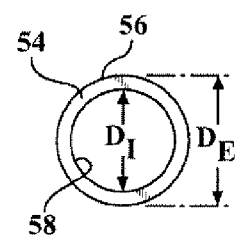
FIG. 7B is an end view of FIG. 7A.
Figure 8A:
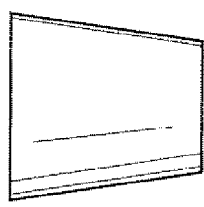
FIG. 8A is a side view of an alternative compression transmission device design.
Figure 8B:
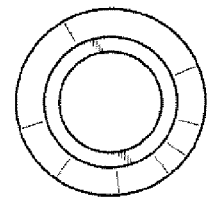
FIG. 8B is an end view of FIG. 8B.
Figure 9A:
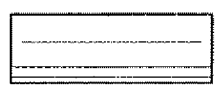
FIG. 9A is a side view of an alternative compression transmission device design.
Figure 9B:
FIG. 9B is an end view of FIG. 9A.
Figure 10A:
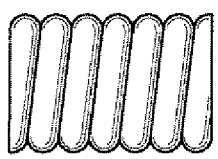
FIG. 10A is aside view of an alternative compression transmission device design.
Figure 10B:
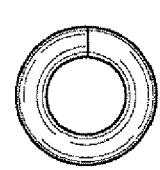
FIG. 10B is an end view of FIG. 10A.
Figure 11A:
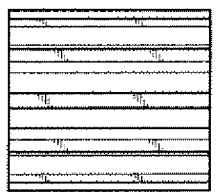
FIG. 11A is a side view of an alternative compression transmission device design.
Figure 11B:
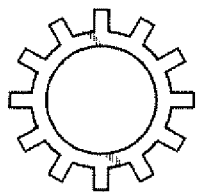
FIG. 11B is an end view of FIG. 11A.

The compression transmission device 54 can have a circular or non-circular cross section, and may be comprised of a single or a plurality of parts. As shown in the compression transmission device 54 design examples in FIGS. 7A-11B, though not exhaustive, the device can include straight or tapered sides as shown in FIGS. 7A-8B, a smooth exterior surface or an exterior surface with protrusions as shown in FIGS. 7B and 11B, a semi-circular cross section as shown in FIG. 9A, and be comprised of a spring or helical coil as shown in FIG. 10A and 10B. The compression transmission device 54 could also include partially tapered sides, a flange on one or both ends, a narrowed central diameter, an expanded central diameter (barrel shaped), and threads on the interior and/or exterior surface. The device can also be comprised of mesh, a plurality of cylindrical discs, of two parts each having a semi-circular cross section, or of a single piece having a partially circular cross section. Further, the device can be perforated, ribbed or corrugated, resorbable, expandable, or drug eluting. All compression transmission devices 54 shroud the fastener 22, thus preventing osseointegration onto the fastener 22. This allows for ease of fastener 22 removal in cases of hardware explantation. Further, the compression transmission devices 54 which are elastic, or store energy, will return to their uncompressed shapes as fastener 22 removal is initiated. This will aid in the removal of bony integration, and ultimately in the removal of all hardware.

The compression transmission device 54 transmits the compressional load of the threaded fastener 22 to the intramedullary nail 20 during fixation, rather than relying on fastener 22 to bone 24 purchase for fixation. Thus, this device can be used in patients with poor bone 24 quality (e.g., secondary to osteoporosis, diabetes, etc.), with unstable fractures (e.g., secondary to complex fractures, exceptionally high or low fractures that traditionally would not be treated with intramedullary nailing, etc.), with only one stable cortex 28 (complex fractures, tumor resections, etc.), or with limited intramedullary contact as would occur in unreamed nailing. The use of the compression transmission device 54 with the fastener 22 improves the tactile sensation experienced by the surgeon as the fastener 22 is installed into the intramedullary nail 20 because the surgeon will feel a hard stop as the fastener 22 head 44 and nail 20 compress the compression transmission device 54.

Figure 2:
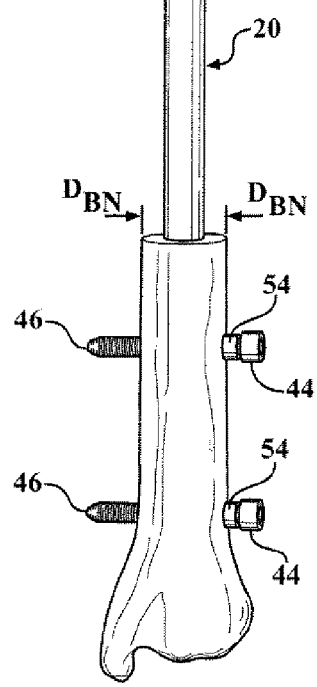
FIG. 2 is a front view of the bores disposed in the intramedullary nail.
Figure 2:
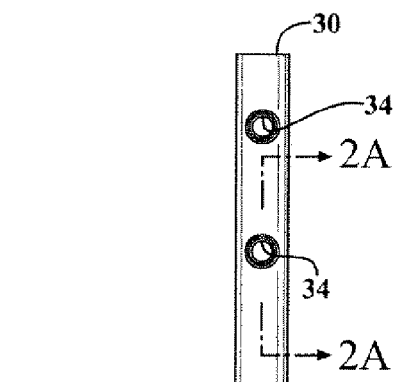
Figure 2A:
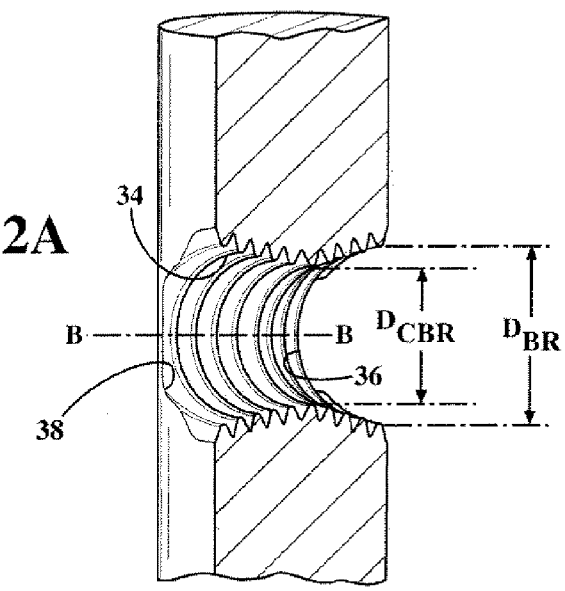
FIG. 2A is a sectional perspective view taken along line 2A-2A of FIG. 2.
Figure 5:
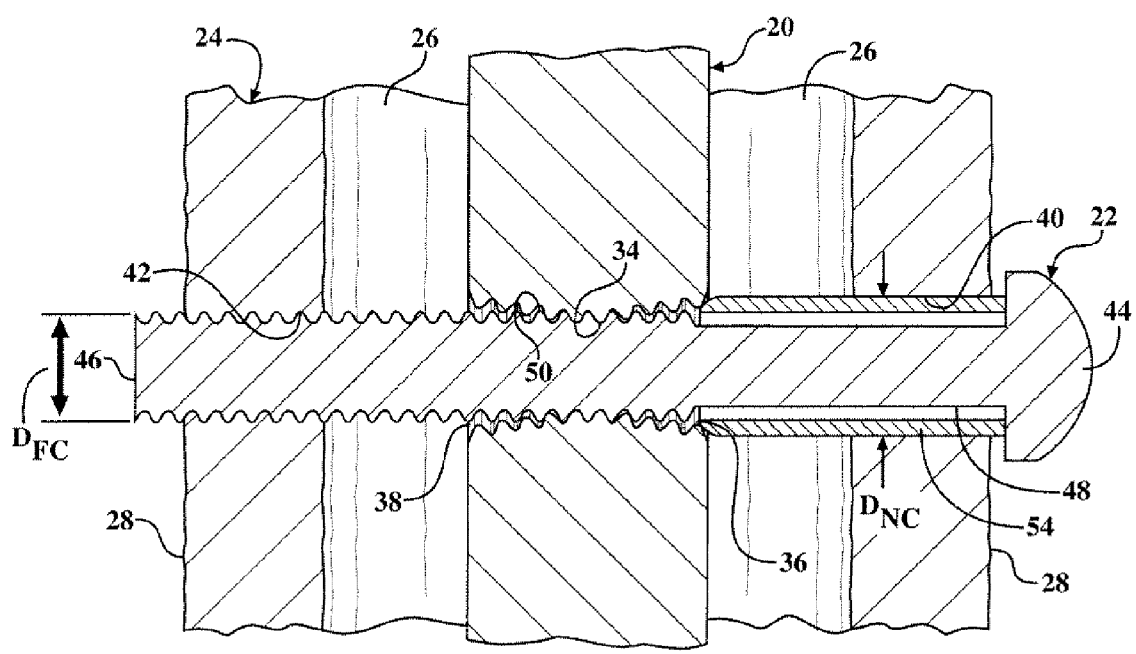
FIG. 5 is an enlarged cross-sectional view of the a fastener extending through the compression transmission device and the intramedullary nail and through the far cortex hole and threadedly engaging the bore.
Figure 6:
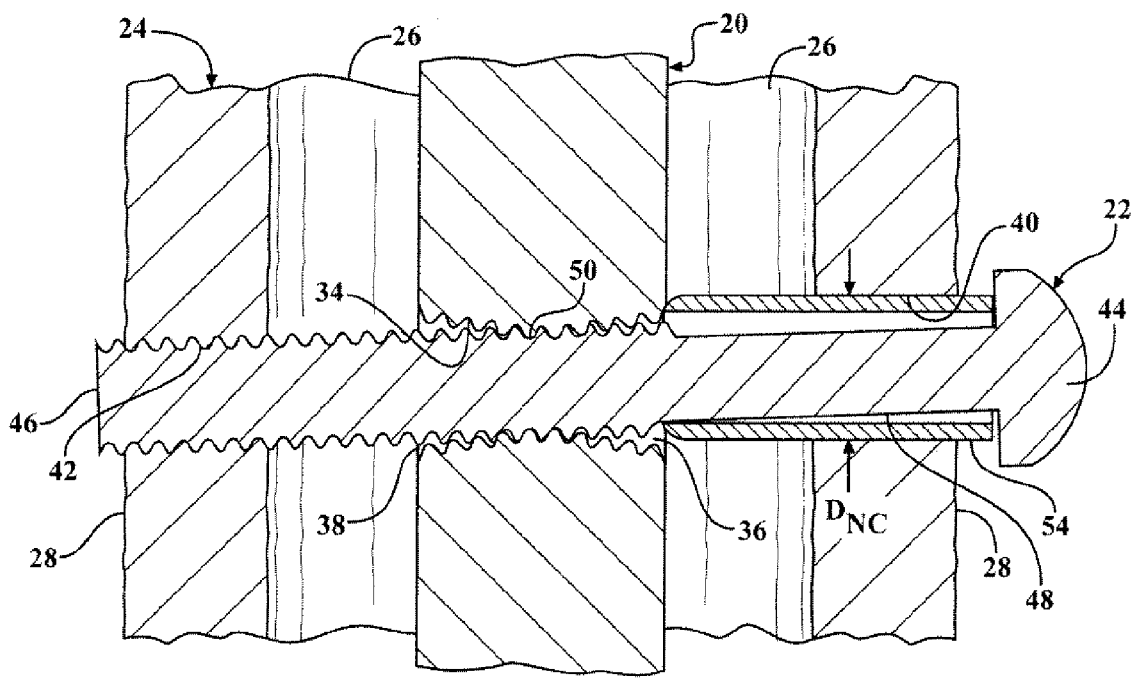
FIG. 6 is a cross-sectional view like FIG. 5 but with the fastener skewed relative to the bore axis and eccentric relative to the interior space of the compression transmission device.

As shown in FIG. 2A, the bore diameter $D_{BR}$ increases from the central bore diameter $D_{CBR}$ to the near opening 36 and from the central bore diameter $D_{CBR}$ to the far opening 38 for allowing the fastener axis A to be skewed relative to the bore axis B while remaining threadedly engaged. This facilitates fastener 22 installation by allowing for more room for error by the surgeon as the fastener 22 will insert and threadedly engage the bore 34 even if the fastener axis A is not parallel to the bore axis B. Alternatively, the bore diameter $D_{BR}$ can be consistent from the central bore diameter $D_{CBR}$ to the near opening 36 and from the central bore diameter $D_{CBR}$ to the far opening 38. The interior space of the compression transmission device 54 is greater than the compression portion diameter $D_{CP}$ of the fastener 22 for providing space at least partially about the threaded fastener 22 for allowing the fastener axis A to be variously disposed, i.e., concentric, eccentric, and/or skewed, relative to the interior space. Thus, the compression transmission device 54 is independent of the fastener 22, i.e., there is no interdigitation of the compression transmission device 54 and the fastener 22. A fastener 22 with a compression portion 48 having a compression portion diameter $D_{CP}$ being smaller than the threaded portion diameter $D_{TP}$ allows for the use of a compression transmission device 54 having a smaller interior space while still allowing the fastener axis A to be disposed eccentrically relative to the interior space. Allowing the fastener axis A to be variously disposed relative to the interior space of the compression transmission device 54 and the bore axis B improves ease of installation of the fastener 22 in the intramedullary nail 20, resulting in faster surgical procedures. This results in a decrease in radiation exposure due to successful fastener 22 implantation on initial attempts. The compression transmission device 54 maintains a fixed predetermined angle relationship between the fastener 22 and the intramedullary nail 20 once installed and compressed, minimizing micro-movements of the nail 20.

The subject invention also includes a method for implanting an intramedullary nail 20 into a medullary canal 26 surrounded by a cortex 28 of a bone 24 having a bone diameter $D_{BN}$ comprising the steps of creating a bore 34 with threads and having a bore axis B extending between a near opening 36 and a far opening 38 transverse to the intramedullary nail 20, the bore 34 having a bore diameter $D_{BR}$ including a central bore diameter $D_{CBR}$ disposed centrally between the near opening 36 and the far opening 38 of the bore 34 in the intramedullary nail 20 wherein the bore diameter $D_{BR}$ increases from the central bore diameter $D_{CBR}$ to the near opening 36 and from the central bore diameter $D_{CBR}$ to the far opening 38 for allowing the fastener axis A to be skewed relative to the bore axis B while remaining threadedly engaged.

Using fluoroscopy or a targeting jig, locating the bore 34 and forming a near cortex hole 40 with a near cortex hole diameter $D_{NC}$ in the cortex 28 before using the nail 20 or jig as a guide to form a far cortex hole 42 with a far cortex hole diameter $D_{FC}$ in the cortex 28 preferably being equal, as illustrated, though it may be unequal, to the central bore diameter $D_{CBR}$ with both in radially overlapping relationship to the bore 34 and with the near cortex hole diameter $D_{NC}$ being greater than the far cortex hole diameter $D_{FC}$.

Providing a threaded fastener 22 including a head 44 and an end 46 with a compression portion 48 having a compression portion diameter $D_{CP}$ and a threaded portion 50 having a threaded portion diameter $D_{TP}$ extending along a fastener axis A therebetween, where the threaded portion diameter $D_{TP}$ is preferably equal, as illustrated, though it may be unequal, to the far cortex hole diameter $D_{FC}$ and the central bore diameter $D_{CBR}$. Further providing the threaded fastener 22 with the compression portion 48 having the compression portion diameter $D_{CP}$ being smaller than the threaded diameter or equal to threaded portion diameter $D_{TP}$, the compression portion 48 being either unthreaded between the head 44 and the threaded portion 50, threaded with threads continuing into the threaded portion 50, or unthreaded between the head 44 and the threaded portion 50 and the threaded fastener 22 including a second unthreaded portion 52 adjacent to the end 46.

The method of implantation further includes providing a compression transmission device 54 being cylindrical or non-cylindrical and including an exterior 56 having an exterior diameter $D_E$ and an interior 58 having an interior diameter $D_I$ defining an interior space for transmitting the compressional load of the threaded fastener 22 to the intramedullary nail 20, inserting the compression transmission device 54 into engagement with the near cortex hole 40 to prevent movement of the compression transmission device 54 relative to the near cortex hole 40, and extending the threaded fastener 22 through the compression transmission device 54 and the intramedullary nail 20 and through the far cortex hole 42 to extend transversely to the intramedullary nail 20 and threadedly engage the bore 34 to fixate the intramedullary nail 20 within the medullary canal 26.

Providing the compression transmission device 54 with the exterior diameter $D_E$ of a sufficient size to allow for mechanical strength without excessively weakening the bone 24 and an interior space being greater than the compression portion diameter $D_{CP}$ of the threaded fastener 22 provides space at least partially about the threaded fastener 22 and allows the fastener axis A to be variously disposed, i.e., eccentric, concentric, and/or skewed, relative to the interior space.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A nail-fastener apparatus for implantation into the medullary canal (26) surrounded by the cortex (28) of a bone (24) including a near cortex hole (40) having a near cortex hole diameter ($D_{NC}$) and a far cortex hole (42) having a far cortex hole diameter ($D_{FC}$) and with the near cortex hole diameter ($D_{NC}$) being greater than the far cortex hole diameter ($D_{FC}$) comprising;

an intramedullary nail (20) extending between a top end (30) and a bottom end (32) and defining a bore (34) extending transverse to said intramedullary nail (20) for insertion into the medullary canal (26) in the bone (24) surrounded by the cortex (28), a threaded fastener (22) including a head (44) and an end (46) with a compression portion (48) and a threaded portion (50) extending along a fastener axis (A) therebetween, said compression portion (48) having a compression portion diameter ($D_{CP}$) and said threaded portion (50) having a threaded portion diameter ($D_{TP}$) for extending through the near cortex hole (40) and the far cortex hole (42) both holes (40, 42) radially overlapping said bore (34) with said threaded portion (50) threadedly engaging said bore (34), a compression transmission device (54) having an exterior (56) and an interior (58) defining an interior space for transmitting the compressional load of said threaded fastener (22) to said intramedullary nail (20) during fixation and contacting the near cortex hole (40) for preventing movement of said compression transmission device (54) relative to the near cortex hole (40), and characterized by, said interior space being greater than said compression portion diameter ($D_{CP}$) of said fastener (22) for providing space at least partially about said threaded fastener (22) for allowing said fastener axis (A) to be variously disposed relative to said interior space.

2. An apparatus as set forth in claim 1 wherein said bore (34) is threaded and has a bore axis (B) extending between a near opening (36) and a far opening (38) transverse to said intramedullary nail (20) and having a bore diameter ($D_{BR}$).

3. An apparatus as set forth in claim 2 wherein said bore diameter ($D_{BR}$) includes a central bore diameter ($D_{CBR}$) disposed centrally between said near opening (36) and said far opening (38) of said bore (34).

4. An apparatus as set forth in claim 3 wherein said bore diameter ($D_{BR}$) increases from said central bore diameter ($D_{CBR}$) to said near opening (36) and from said central bore diameter ($D_{CBR}$) to said far opening (38) for allowing said fastener axis (A) to be skewed relative to said bore axis (B) while remaining threadedly engaged.

5. An apparatus as set forth in claim 1 wherein said compression portion diameter ($D_{CP}$) is smaller than said threaded portion diameter ($D_{TP}$).

6. An apparatus as set forth in claim 1 wherein said compression portion diameter ($D_{CP}$) is equal to said threaded portion diameter ($D_{TP}$).

7. An apparatus as set forth in claim 1 wherein said compression portion (48) is unthreaded between said head (44) and said threaded portion (50).

8. An apparatus as set forth in claim 1 wherein said compression portion (48) is threaded with threads continuing into said threaded portion (50).

9. An apparatus as set forth in claim 7 wherein said threaded fastener (22) includes an unthreaded portion adjacent to said end (46).

10. An apparatus as set forth in claim 3 wherein the far cortex hole diameter ($D_{FC}$) is equal to said central bore diameter ($D_{CBR}$).

11. An apparatus as set forth in claim 10 wherein said threaded portion diameter ($D_{TP}$) being equal to the far cortex hole diameter ($D_{FC}$) and said central bore diameter ($D_{CBR}$).

12. An apparatus as set forth in claim 1 further comprising said threaded fastener (22) extending through said compression transmission device (54) and said intramedullary nail (20) and the far cortex hole (42) so as to extend transversely to said intramedullary nail (20) for threadedly engaging said bore (34) and fixating said intramedullary nail (20) within the medullary canal (26).

13. An apparatus as set forth in claim 1 wherein said compression transmission device (54) is cylindrical and said exterior (56) of said compression transmission device (54) having an exterior diameter ($D_E$) and said interior (58) of said compression transmission device (54) having an interior diameter ($D_I$).

14. A method for implanting an intramedullary nail (20) into the medullary canal (26) surrounded by the cortex (28) of the bone (24) comprising the steps of;
creating a bore (34) in the intramedullary nail (20) extending transverse to the intramedullary nail (20) including threads,
forming a near cortex hole (40) in the cortex (28) and a far cortex hole (42) in the cortex (28) both in radially overlapping relationship to the bore (34),
providing a threaded fastener (22) including a head (44) and an end (46) with a compression portion (48) having a compression portion diameter ($D_{CP}$) and a threaded portion (50) having a threaded portion diameter ($D_{TP}$) extending along a fastener axis (A) therebetween,
providing a compression transmission device (54) having an exterior (56) and an interior (58) defining an interior space for transmitting the compressional load of the threaded fastener (22) to the intramedullary nail (20),
inserting a compression transmission device (54) into engagement with a near cortex hole (40) to prevent movement of the compression transmission device (54) relative to the near cortex hole (40),
extending the threaded fastener (22) through the compression transmission device (54) and the intramedullary nail (20) and through a far cortex hole (42) to extend transversely to the intramedullary nail (20) and threadedly engaging the bore (34) to fixate the intramedullary nail (20) within the medullary canal (26),
and characterized by,
providing the compression transmission device (54) with the interior space being greater than the compression portion diameter ($D_{CP}$) of the threaded fastener (22) for providing space at least partially about the threaded fastener (22) for allowing the fastener axis (A) to be variously disposed relative the interior space.

15. A method as set forth in claim 14 including creating the bore (34) having a bore axis (B) extending between a near opening (36) and a far opening (38) transverse to the intramedullary nail (20) and having a bore diameter ($D_{BR}$) including a central bore diameter ($D_{CBR}$) disposed centrally between the near opening (36) and the far opening (38) of the bore (34) in the intramedullary nail (20).

16. A method as set forth in claim 15 including creating the bore (34) wherein the bore diameter ($D_{BR}$) increases from the central bore diameter ($D_{CBR}$) to the near opening (36) and from the central bore diameter ($D_{CBR}$) to the far opening (38) for allowing the fastener axis (A) to be skewed relative to the bore axis (B) while remaining threadedly engaged.

17. A method as set forth in claim 14 including providing a threaded fastener (22) with the compression portion (48) having a compression portion diameter ($D_{CP}$) being smaller than the threaded portion diameter ($D_{TP}$).

18. A method as set forth in claim 14 including providing a threaded fastener (22) with the compression portion (48) having a compression portion diameter ($D_{CP}$) being equal to the threaded portion diameter ($D_{TP}$).

19. A method as set forth in claim 14 including providing the threaded fastener (22) with the compression portion (48) being unthreaded between the head (44) and the threaded portion (50).

20. A method as set forth in claim 14 including providing the threaded fastener (22) with the compression portion (48) being threaded with threads continuing into the threaded portion (50).

21. A method as set forth in claim 19 including providing the threaded fastener (22) with a second unthreaded portion (52) adjacent to the end (46).

22. A method as set forth in claim 16 including forming the near cortex hole (40) with a near cortex hole diameter ($D_{NC}$).

23. A method as set forth in claim 22 including forming the far cortex hole (42) having a far cortex hole diameter ($D_{FC}$) equal to the central bore diameter ($D_{CBR}$) and less than the near cortex hole diameter ($D_{NC}$).

24. A method as set forth in claim 23 including forming the near cortex hole (40) with the greater diameter before forming of the far cortex hole (42) with the lesser diameter.

25. A method as set forth in claim 23 including providing the threaded fastener (22) having the threaded portion diameter ($D_{TP}$) being equal to the far cortex hole diameter ($D_{FC}$) and the central bore diameter ($D_{CBR}$).

26. A method as set forth in claim 14 including inserting the compression transmission device (54) into engagement with the near cortex hole (40) to prevent movement of the compression transmission device (54) relative to the near cortex hole (40).

27. A method as set forth in claim 14 including providing the compression transmission device (54) being cylindrical and including an exterior (56) having an exterior diameter ($D_E$) and the interior (58) having an interior diameter ($D_I$).

* * * * *